US006054310A

United States Patent [19]

Kim et al.

[11] Patent Number: 6,054,310

[45] Date of Patent: Apr. 25, 2000

[54] CONTINUOUS FED-BATCH DEGRADATION OF DECONTAMINATING SOLUTION 2 (DS2)

[75] Inventors: Michael H. Kim, Ellicott City; Joseph J. DeFrank, Bel Air, both of Md.

[73] Assignee: The United States of America as represented by the Secretary of the Army, Washington, D.C.

[21] Appl. No.: 09/195,113

[22] Filed: Nov. 18, 1998

[51] Int. Cl.[7] .......................... C07C 1/02

[52] U.S. Cl. .......................... 435/252.4; 435/252.2; 435/262

[58] Field of Search .......................... 435/252.4, 252.5, 435/262, 262.5

[56] References Cited

U.S. PATENT DOCUMENTS

| | | | |
|---|---|---|---|
| 4,537,682 | 8/1985 | Wong-Chong | 210/611 |
| 5,686,291 | 11/1997 | Ohkawa et al. | 435/252.1 |

*Primary Examiner*—David A. Redding
*Attorney, Agent, or Firm*—Vincent J. Ranucci

[57] ABSTRACT

A process for biodegradation of an amine compound by contacting the amine compound with a consortium of microorganisms effective for consuming carbon and nitrogen components of the amine compound under aerobic conditions, wherein the enzymatically degraded the amine compound forms an ammonia residue, nitrifying the ammonia residue under aerobic conditions, wherein the ammonia residue forms nitrite and nitrate residues and denitrifying the compound with the addition of a supplementary carbon source under anoxic conditions. The amine compound may be DS2 or similar amine structures. The microorganisms include *Bacillus circulans,* the genera Nitrosomonas, and the genera Nitrobacter. The process is a continuous-fed process in a bioreactor. A composition of microorganisms comprising *Bacillus circulans,* the genera Nitrosomonas, the genera Nitrobacter, and facultative heterotrophic denitrifiers effective to degrade DS2 also is disclosed.

20 Claims, 6 Drawing Sheets

CONTINUOUS FED-BATCH DEGRADATION OF DECONTAMINATING SOLUTION 2 (DS2)

GOVERNMENT INTEREST

The invention described herein may be manufactured, licensed, and used by or for the U.S. Government.

BACKGROUND OF THE INVENTION

1. Field of the Invention

The present invention relates to the biodegrading of amine compounds. More particularly, the present invention is a process for biodegrading diethylenetriamine. Most particularly, the present invention provides for the process for the continuous fed-batch biodegradation of Decontamination Solution 2 (DS2).

2. Brief Description of the Prior Art

The safe disposal of hazardous wastes is a significant societal problem. Private industry and governmental agencies must adhere to ever increasing strict laws and regulations regarding the disposal of these hazardous wastes. As such, innovative processes are needed to reduce or eliminate hazardous waste.

Biodegradation of organic compounds using microorganisms is known. Organisms use chemicals as a source of nutrient for survival. Depending on the elemental composition, the chemicals may be used as a source of carbon, nitrogen, or phosphorous for cell propagation. In using the chemicals, the microorganisms may convert toxic chemicals into benign chemical forms. However, microorganisms must possess the necessary enzymatic systems for particular chemical compositions.

Decontamination Solution 2, or DS2, is a chemical warfare decontaminating solution used by the United States Army. DS2 contains approximately 70% diethylenetriamine (DETA), 28% ethylene glycol monomethyl ether (EGME), and 2% NaOH by weight, and is used for decontaminating a variety of chemical warfare agents. However, DS2 is toxic, flammable and hazardous to the environment. EGME is teratogenic, and the secondary amine structure in DETA possess a possible health hazard from conversion to a potential N-nitrosoamine carcinogen. DS2 is extremely resistant to biodegradation, particularly with regard to the DETA component of the solution.

Low molecular weight primary, secondary and tertiary amines have been shown as a sole source of carbon for *Pseudomonas aminovorans* and readily oxidized by cell extracts (Eady et. al. 1971). However, higher molecular weight secondary linear and cyclic amines have been shown to be recalcitrant and toxic to microorganisms (Emtiazi and Knapp, 1994). Several forms of secondary or tertiary amine compounds which contain one or more carboxylic groups have been shown to be biodegraded by *Chelatobacter heintzii* ATCC 29600 and other bacterial species, and the responsible genes have been cloned and expressed (Knobel et. al., 1996). However, the biodegradability of secondary or tertiary amines which lack such carboxylic groups as in DETA is not known.

In view of the foregoing, degradation of DS2, particularly the DETA component of DS2, in a bioreactor or in situ is desirable.

The present invention addresses these needs.

SUMMARY OF THE INVENTION

The present invention provides a process for biodegradation of an amine compound comprising the steps of (a) contacting the amine compound with a consortium of microorganisms effective for consuming carbon and nitrogen components of the amine compound under aerobic conditions, wherein the enzymatically degraded the amine compound forms an ammonia residue; (b) nitrifying the ammonia residue under aerobic conditions, wherein the ammonia residue forms nitrite and nitrate residues; and (c) denitrifying the compound with the addition of a supplementary carbon source under anoxic conditions.

In another aspect of the present invention, there is provided a composition of microorganisms comprising *Bacillus circulans,* the genera Nitrosomonas, the genera Nitrobacter, and facultative heterotrophic denitrifiers effective to degrade DS2.

The process and composition of the present invention are extremely valuable in the field of the degradation of DS2 and other amine compounds. Other and further advantages of the present invention are set forth in the description and appended claims.

DETAILED DESCRIPTION OF THE PREFERRED EMBODIMENTS

Figure 1:
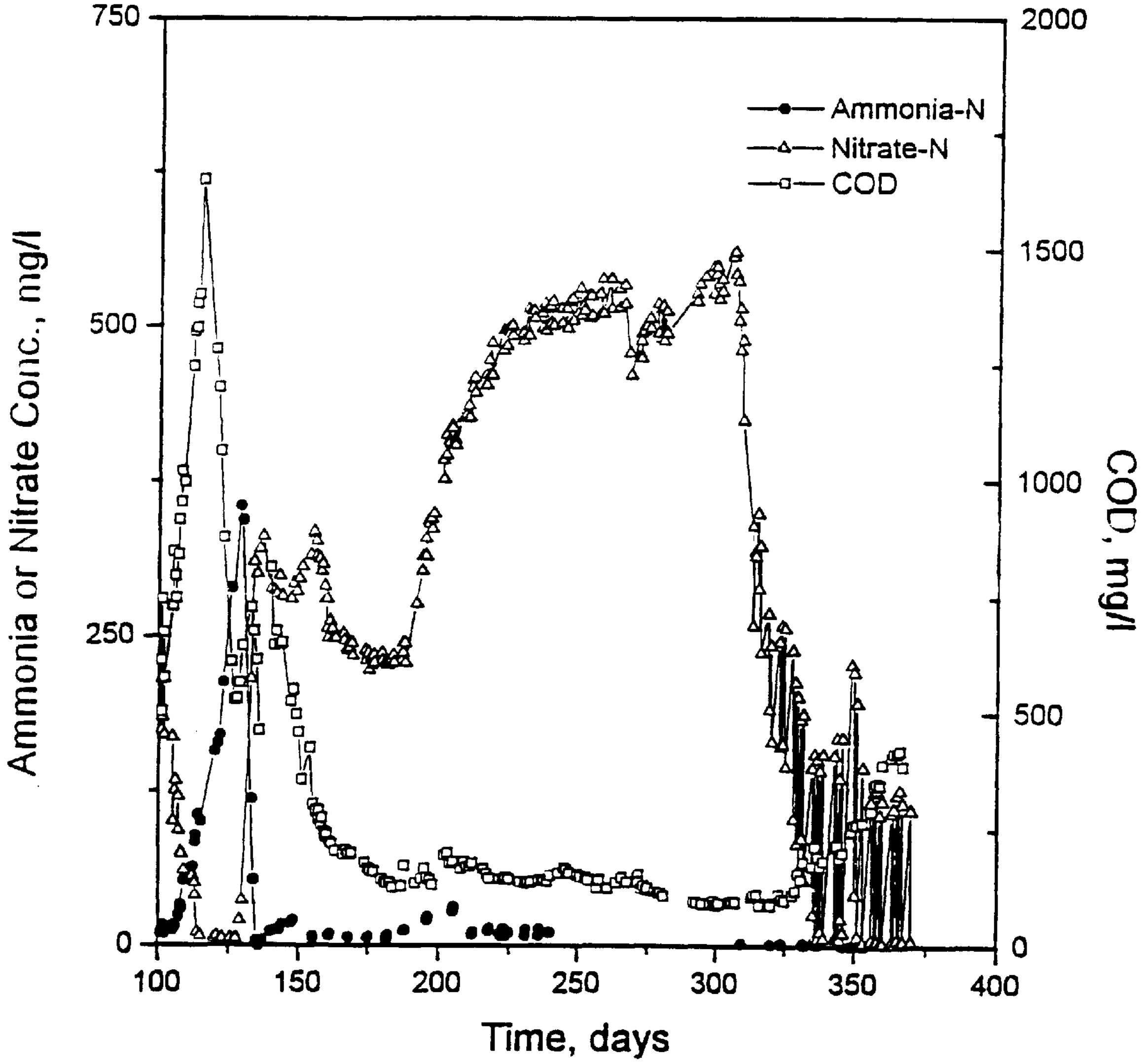
FIG. 1 is a graph illustrating the overall operation of a fed-batch bioreactor at the hydraulic retention time of 16 day for DS2 degradation and total nitrogen removal, with the DS2 feed concentration progressively increase from 0.1% to 1.0%.

The present invention is a process for biodegradation of an amine compound and a composition useful in that process. The process and composition allow for the degradation of amine compounds that are environmentally toxic, especially chemical compounds containing DETA such as DS2. The process allows a continuous process for the degradation of the amine compounds. The composition includes an enriched consortium of microorganisms enzymatically capable of degrading DS2 comprising *Bacillus circulans,* and other like microorganisms for the degradation of DETA, and further comprising microorganisms from the genera Nitrosomonas, the genera Nitrobacter, and facultative heterotrophic denitrifiers.

A process for biodegradation of an amine compound includes the steps of contacting the amine compound with a consortium of microorganisms effective for consuming carbon and nitrogen components of the amine compound under aerobic conditions. During this step, the enzymatically degraded amine compound forms an ammonia residue. Another step includes nitrifying the ammonia residue under aerobic conditions to form nitrite and nitrate residues. Additional steps of the process include denitrifying the compound with the addition of a supplementary carbon source under anoxic conditions. In a preferred embodiment, the amine compound is contacted with the consortium of microorganisms sequentially with the denitrification of the compound with the addition of a supplementary carbon source under anoxic conditions.

Preferably, the amine compound comprises diethylenetriamine (DETA). More preferably, the amine compound further comprises ethylene glycol monomethyl ether (EGME). Most preferably, the amine compound comprises DS2. Additionally, the amine compound may comprise an explosive-based composition, such as a nitrocellulose, propellent, and other similar chemical structures.

The consortium of microorganisms of the present invention includes *Bacillus circulans*, and/or other like microorganisms for the degradation of the amine compound into ammonia, water and carbon dioxide. Similarity Index analysis for the microorganisms of the present invention yielded a microorganism identification rated as excellent of *Bacillus circulans*, with a similarity index of 0.839. The ammonia resulting from the DS2 degradation, however, may cause an inhibition of further DS2 degradation. The term ammonia referred to herein encompasses those compounds normally associated with the term ammonia, including both $NH_3$ and the ion $NH_4^+$ that normally exists in aqueous solution under the thermodynamic equilibrium conditions, shown in the formula:

$$NH_4^+ + OH— \leftrightarrows NH_3 + H_2O$$

The nitrifying component of the consortium of microorganisms further includes the genera Nitrosomonas as a nitrifying agent for oxidizing ammonia to nitrite. Representative examples of the genera Nitrosomonas used as a nitrifying agent in the present invention include those genera Nitrosomonas disclosed in U.S. Pat. No. 4,537,682 (Wong-Chong), dated Aug. 27, 1985, the disclosure of which is herein incorporated by reference. These genera Nitrosomonas include such species as *Nitrosomonas europea*. During the nitrifying of ammonia to nitrite, one mole of ammonia ($NH_4^+$) is reacted with 1.5 moles of oxygen ($O_2$) to produce one mole of $NO_2^-$, two mole of hydrogen ($H^+$), and one mole of water ($H_2O$).

Additionally, the microorganisms comprise the genera Nitrobacter as a nitrifying agent for oxidizing nitrite to nitrate. Representative examples of the genera Nitrobacter used as a nitrifying agent in the present invention include those genera Nitrobacter also disclosed in U.S. Pat. No. 4,537,682 (Wong-Chong), dated Aug. 27, 1985, the disclosure of which is herein incorporated by reference. These genera Nitrobacter include such species as *Nitrobacter winnnogradski* and *Nitrobacter agilis*. During the nitrifying of nitrite to nitrate, one mole of $NO_2^-$ is reacted with 0.5 moles of oxygen ($O_2$) to produce one mole of $NO_2^-$, two mole of hydrogen ($H^+$), and one mole of water ($H_2O$).

The present invention provides for the addition of a supplementary carbon for the microorganisms. DS2 does not provide an adequate carbon source for the proper functioning of the microorganisms. Preferably, the supplementary carbon source comprises a simple carbon compound such as methanol or a sugar, such as glucose. More preferably the supplementary carbon source comprises a methanol.

The present invention includes a process for simultaneously degrading DS2, nitrifying the mineralized ammonia under aerobic conditions, and denitrifying for nitrogen removal as nitrogen gas with the addition of a supplementary carbon source under anoxic conditions. DS2 degradation and nitrification are simultaneously achieved under aerobic conditions. Denitrification in which microorganisms use nitrate as an alternate terminal electron acceptor to molecular oxygen is used to remove nitrate under air-off periods. An alternating air-on and air-off cycle provides the necessary aerobic and anoxic conditions.

The present invention further includes a DS2 feeding strategy for the continuous fed-batch operation that by-passes potential DS2 toxicities to the enriched consortium of microorganisms. DS2 is continuously fed into a fed-batch bioreactor to provide component carbon, energy, and nitrogen sources under aerobic conditions. With the air supply and DS2 feed paused, methanol was added to provide a carbon sources during the air-off period. The cycle included an eighteen (18) hours air-on period, followed by a six (6) hour air-off period. The aerobic conditions are maintained by bubbling oxygen into the bioreactor containing the amine/carbon compound and microorganisms of the species *Bacillus circulans,* the genera Nitrosomonas, the genera Nitrobacter, and facultative heterotrophic denitrifiers. The amine compound is fed into a bioreactor, preferably continuously. Preferably, DS2 in amounts of from about 0.3% to about 0.7% are mixed with from about 10,000 mg/L to about 14,000 mg/L of microorganisms, or DS2 in amounts of from about 0.8% to about 1.2% with from about 18,000 mg/L to about 22,000 mg/L of microorganisms. The composition of the mixed microorganisms comprises an effective amount of species *Bacillus circulans,* the genera Nitrosomonas, the genera Nitrobacter, and facultative heterotrophic denitrifiers to degrade DS2.

The degradation or mineralization of DS2 components by the consortium of microorganisms is evident in the effluent chemical oxygen demand (COD) of less than 500 mg/L, as compared to 17230 mg/L of the DS2 1% solution feed. As DETA provides the only source of nitrogen in the DS2 feed, the accumulation of ammonia during the DS2 degradation further demonstrated a mineralization of the DETA. The nitrogen content of the DS2 is approximately 41%, which far exceeds a normal requirement of 10% to 15% for microbial growth.

FIG. 1 illustrates the DS2 degradation and total nitrogen removal through nitrification/denitrification. As seen in FIG. 1 is a graph illustrating the overall operation of a fed-batch bioreactor at the hydraulic retention time of 16 day for DS2 degradation and total nitrogen removal, with the DS2 feed concentration progressively increase from 0.1% to 1.0%.

Figure 2:
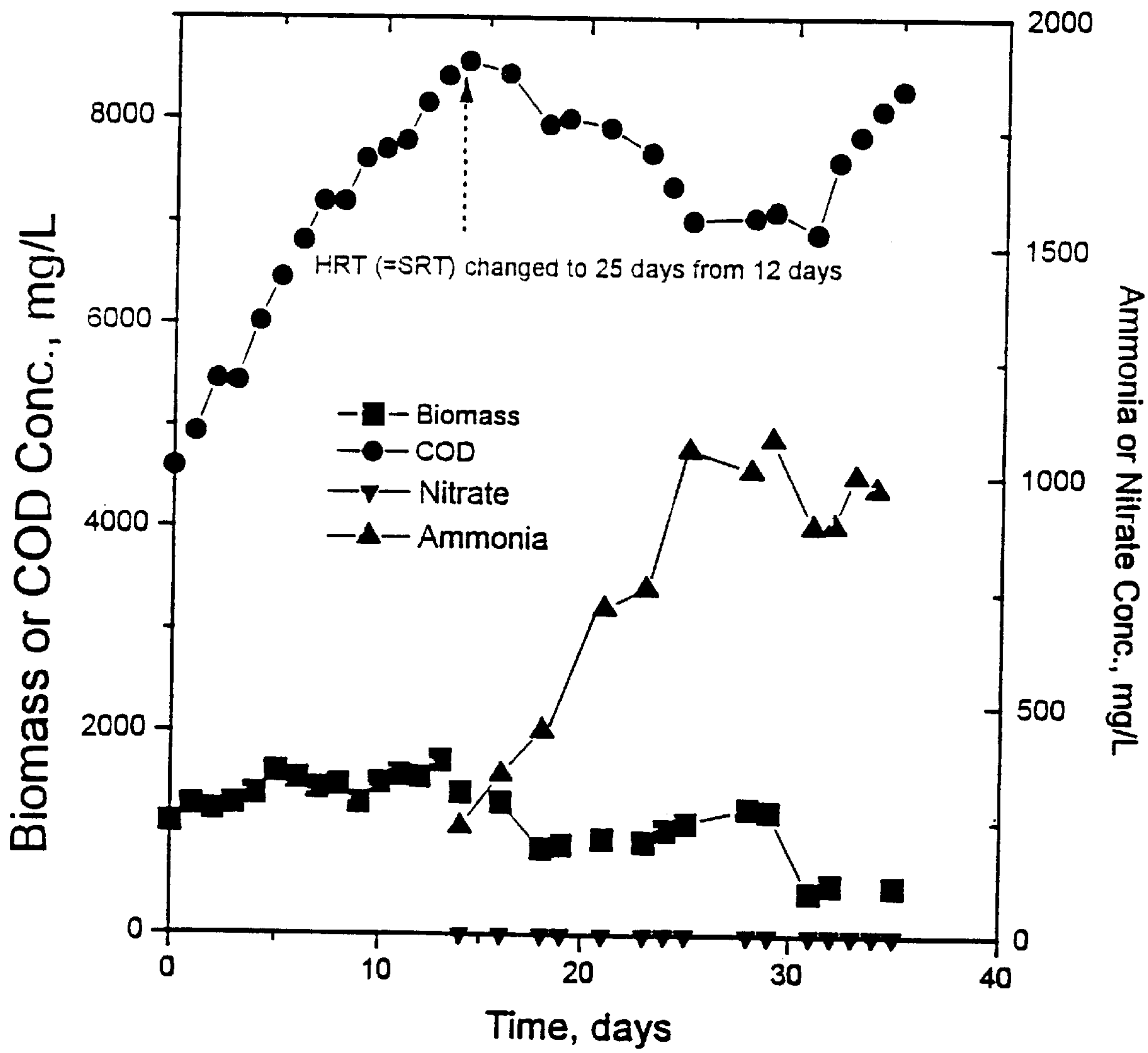
FIG. 2 is a graph illustrating the toxicity of high ammonia concentration of the DS2 degradation.

FIG. 2 shows a graph illustrating the toxicity of high ammonia concentration of the DS2 degradation. The ammonia resulting from the DS2 degradation, unless reduced in concentration, caused an inhibition to the DS2 degradation. At the start-up period of the fed-batch bioreactor, the consortium of microorganisms was not sufficiently acclimated to 1% solution of DS2 at a hydraulic retention time of 16 days, as evidenced by an increase in the effluent COD value. Hydraulic retention time (HRT) of the bioreactor was increased to 24 days to decrease the DS2 loading. A corresponding effluent COD decrease was seen with the reduced hydraulic retention time. However even with the reduced hydraulic retention time, as the ammonia concentration built up without nitrification, the effluent COD increased again, indicating an inhibitory effect of the high ammonia concentration on the DS2 degradation. As seen in FIG. 2, not only does a high ammonia concentration inhibit the DS2 degradation but a high COD also inhibits nitrification.

Figure 3:
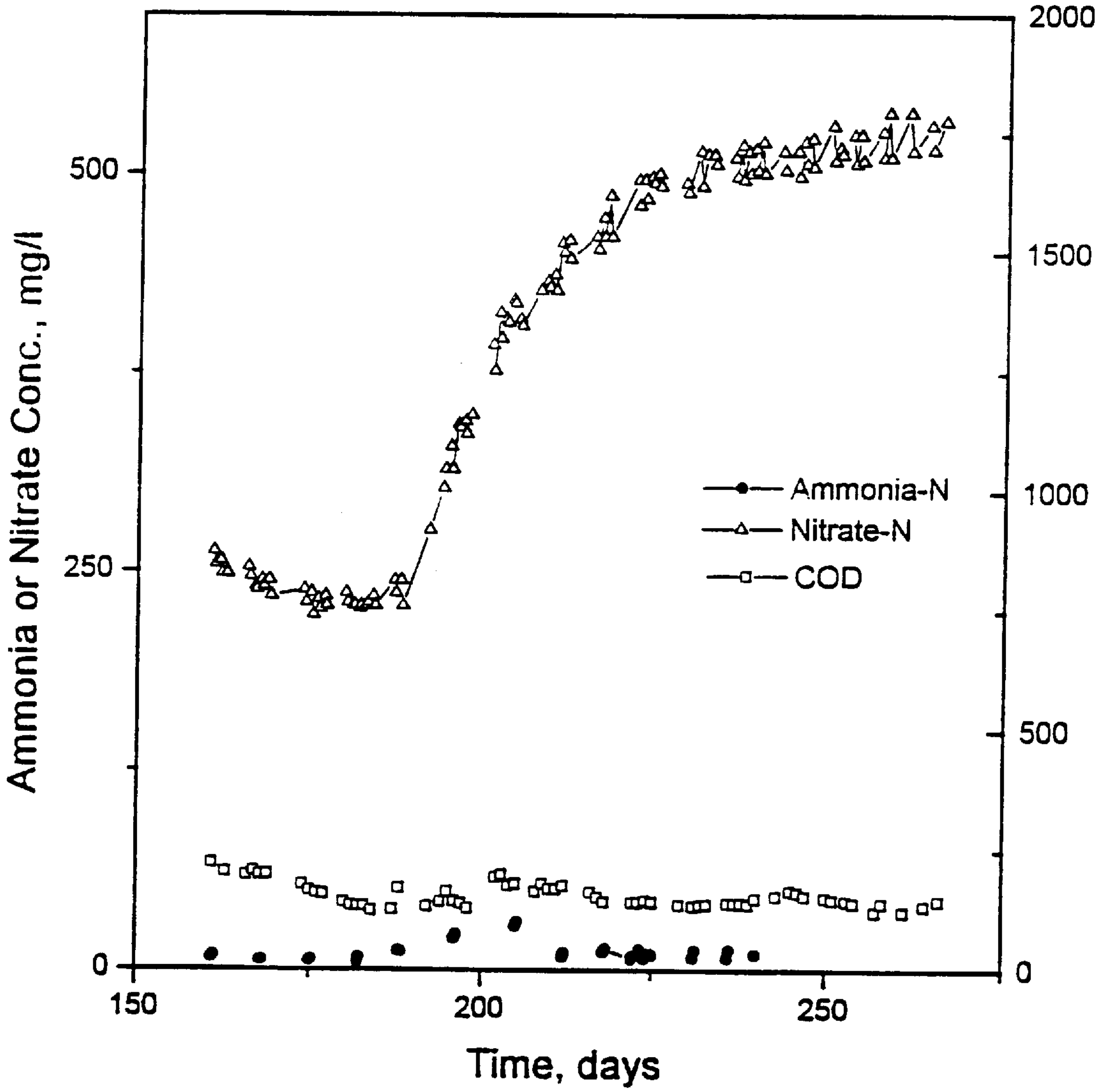
FIG. 3 is a graph illustrating the absence of denitrification using the DS2 as a carbon source during the air-off periods.

In FIG. 3, a graph illustrates the absence of denitrification using the DS2 as a carbon source during the air-off periods. Nitrifiers are chemoautotrophic microorganisms that obtain metabolic energy by oxidizing ammonia to nitrite and to the nitrate. The present invention provides the genera Nitrosomonas for oxidizing ammonia to nitrite and the genera Nitrobacter for oxidizing nitrite to nitrate. The primary carbon source being carbon dioxide. The steady increases in the nitrate concentration with low concentration of both COD and ammonia, shown in FIG. 3, demonstrates the commensal effect of the DS2 degraders and nitrifiers for the DS2 without any apparent inhibition of each other. However, the steady accumulation of nitrate also showed that denitrification was absent in the bioreactor during air-off periods, possibly caused from the inability of the microorganism consortium for denitrification and/or the unsuitability of the DS2 feed as a carbon source for denitrifiers.

Figure 4:
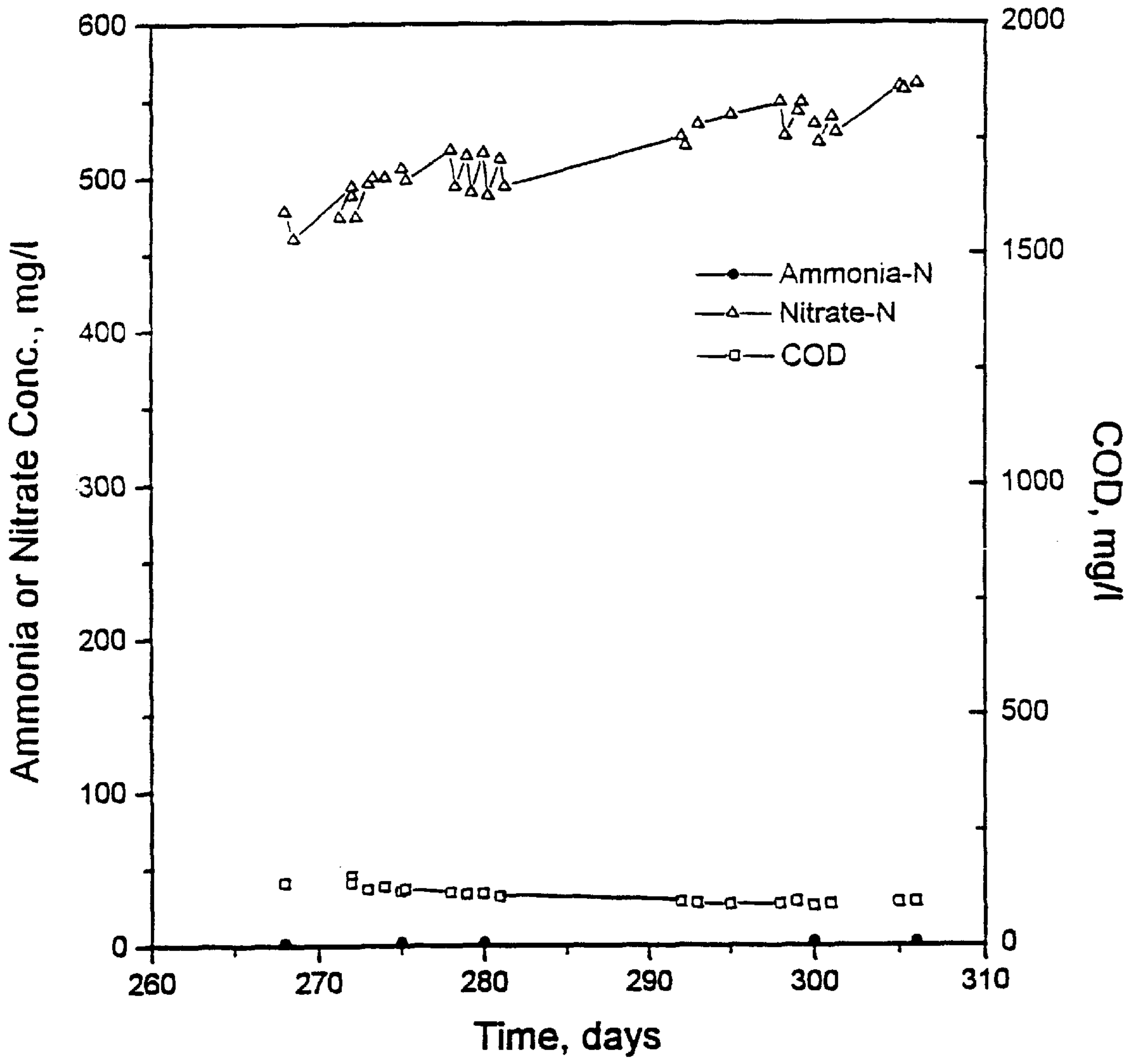
FIG. 4 is a graph illustrating the absence of denitrification during endogenous respiration periods.

FIG. 4 shows a graph illustrating the absence of denitrification during endogenous nitrate respiration (ENR) periods. The DS2 feed was stopped during air-off periods to determine the ENR affect to reduce the nitrate. Microorganisms use cell masses as a carbon source with nitrate as the terminal electron acceptor. The steady increases in nitrate during the discontinuation of DS2 feed during the air-off period demonstrated that the ENR has practically no capacity to reduce the nitrate level. Accordingly, methanol is provided as an alternate carbon source to increase the rate of denitrification during the air-off periods.

Figure 5:
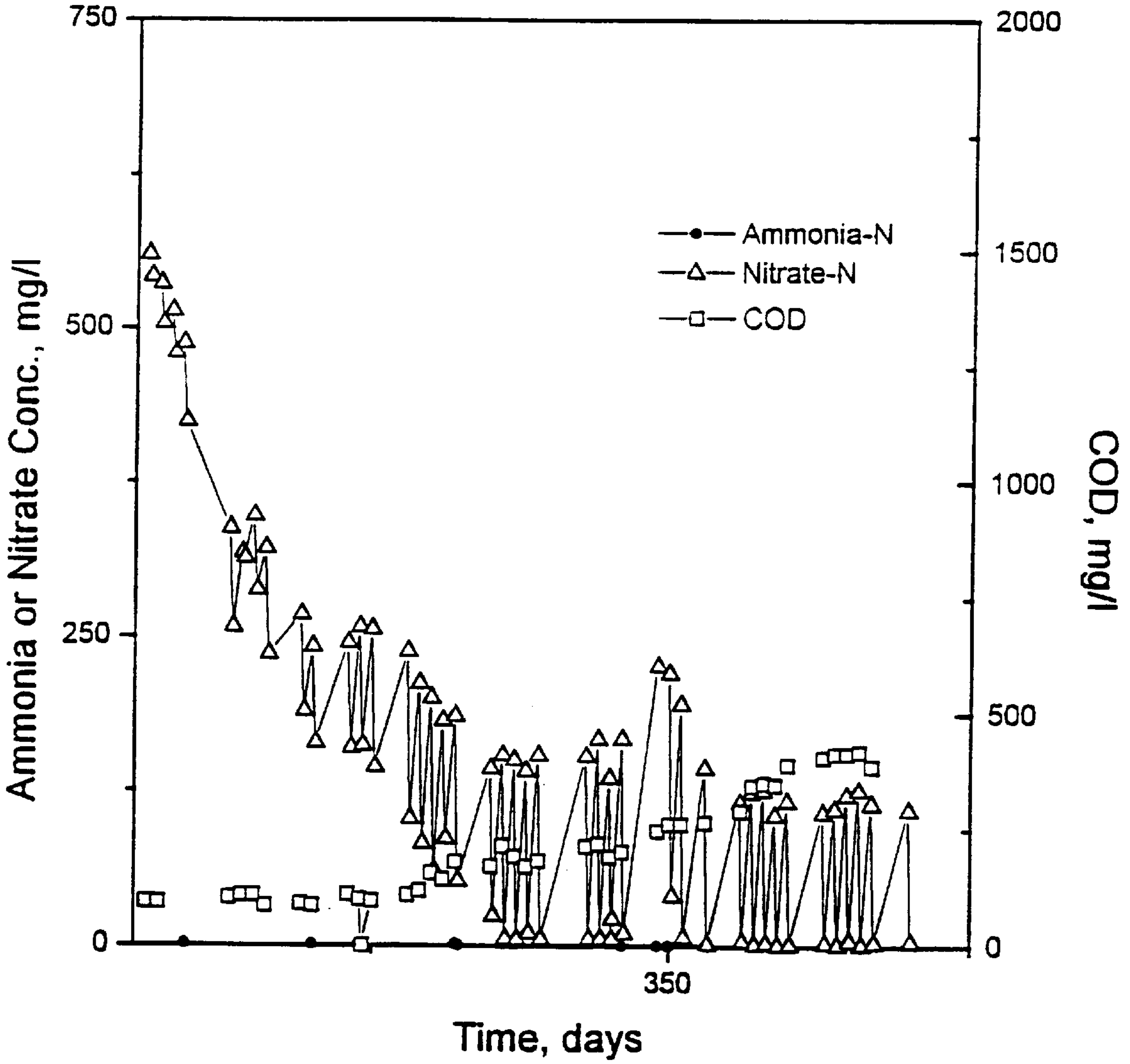
FIG. 5 is a graph illustrating the rapid denitrification with the addition of methanol as a substrate during anoxic periods; and, FIG. 6 is a graph illustrating a set of specific denitrification rates obtained at different initial biomass concentrations.

In FIG. 5, a graph illustrating the rapid denitrification with the addition of methanol as a substrate during anoxic periods. As seen in FIG. 5, the level of nitrate during the air-off period started to decrease immediately after the addition of methanol.

Figure 6:
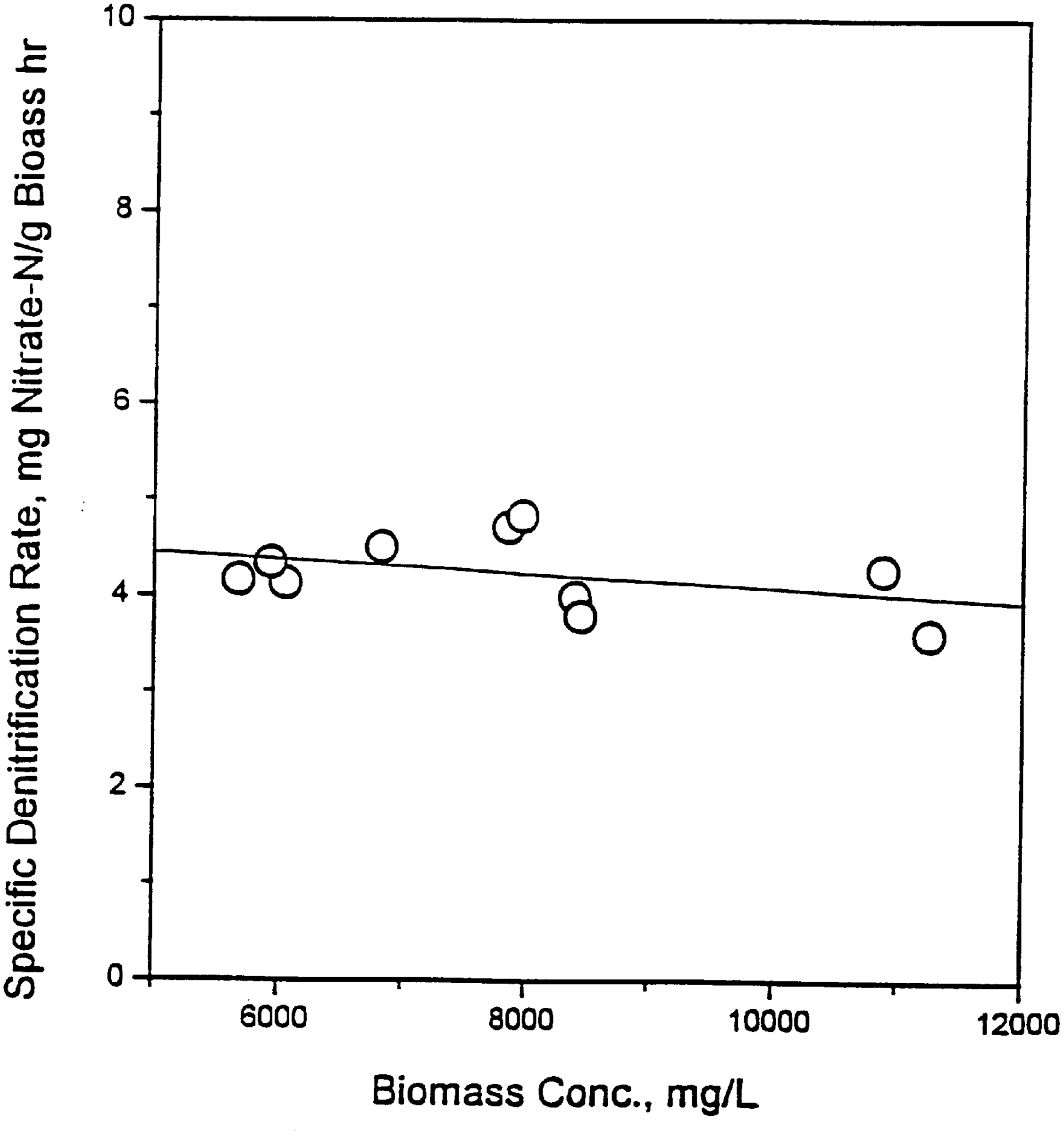

FIG. 6 shows a graph illustrating a set of specific denitrification rates obtained at different initial biomass concentrations ranging from approximately 5000 mg/L to 12000 mg/L during the air-off periods. The specific denitrification rate was essentially constant over the wide range of biomass concentrations tested. This evidenced that denitrifiers were integral members of the microbial consortia to enable the system for the DS2 degradation, nitrification, and denitrification. The carbon requirement as methanol for denitrification was determined to be in the range of 2.6 to 3.6 mg COD equivalent of methanol per mg of nitrate nitrogen.

In operation, simultaneously with the DS2 degradation, nitrification of the mineralized ammonia from the high nitrogen content in DETA occurs. The nitrification product was biologically denitrified for total nitrogen removal with the addition of methanol under air-off conditions.

EXAMPLE 1

An enriched consortium of microorganisms of the species *Bacillus circulans*, the genera Nitrosomonas, and the genera Nitrobacter, and facultative heterotrophic denitrifiers were feed into a bioreactor with a solution of 1% DS2 feed. Oxygen was bubbled into the mixture for an eighteen hour period. Afterward, a six hour period of no oxygen was provided. The procedure was conducted for a 16 day period.

The process allowed 17230 mg/L (equivalent to 1% DS2 in water) COD (chemical oxygen demand) of normally toxic DS2 to be biologically degraded with less than 500 mg/L of residual COD at the hydraulic retention time of 16 days.

One preferred source of "seed" for the microorganisms of the present invention includes second stage conventional wastewater treatment facilities, such as municipal wastewater treatment facilities.

Procedures

Chemical Oxygen Demand (COD): Chemical oxygen demand was determined spectrophotometrically at 620 nm using a potassium dichromate digestion method, known as the Hach Method 8000. The Hach Method 8000 is equivalent to Method 5220C in $18^{th}$ edition of the Standard Methods for the Examination of Water and Wastewater (AWWA, 1992) except that the Hach Method 8000 uses absorbance reading at 600 nm instead of ferrous ammonium sulfate titration for the determination of the remaining potassium dichromate after the digestion.

Ammonia: The amino groups present in DETA showed positive interference for colorimetric analysis of ammonia. Accordingly, for samples containing a significant amount of both ammonia and DETA, the concentration of ammonia was assayed by either dabsylation or dansylation followed by analysis with a high pressure liquid chromatograph (HPLC), made by Beckman Instrument Co. of Palo Alto, Calif. that was equipped with an Ultramex 5 reverse-phase c18 (250×4.6 mm I.D.) and an ultraviolet (UV) detector. For samples containing a negligible amount of DETA, as indicated by a low COD, ammonia was analyzed spectrophotometrically at 650 nm using a salicylate method, known as Hach Method 8155. Hach Method 8155 involves converting ammonia compound to monochloroamine with chlorine, which further reacts with salicylate to form 5-aminosalicylate. The 5-aminosalicylate is oxidized in the presence of a sodium nitroprusside catalyst to form a blue-colored compound, which is measured spectrophotometrically at 655 nm.

Ammonia Determination 1

A sample of 1.0 ml for dabsylation was placed in a 15 ml screw-capped vial, saturated with disodium carbonate, and mixed with 1.0 of 1.8 mg/ml dabsyl chloride in acetone, and heated at 55° C. for two hours. After cooling to room temperature, 0.5 ml of 1.8 mg/ml dabsyl chloride in acetone was added to dabsylation mixture and heated one additional hour at 55° C. After cooling to room temperature, dabsylated ammonia was extracted twice with 1 ml of n-hexane:n-butanol (1:1). The organic layers were combined, washed twice with 2 ml of deionized water, and dehydrated over anhydrous sodium sulfate. A 25 $\mu$l aliquot of clear extract was injected into the HPLC column and monitored at 425 nm. The mobile phases had of 95% ethanol:acetonitrile:water (6:6:7) for dabsylated samples and acetonitrile:water containing 0.005 M 1-pentanesulphonic acid sodium salt (72%:28%), pH adjusted to 3.5 with acetic acid. The flow rate of mobile phase was 1.0 ml for dabsylated sample analysis.

Ammonia Determination 2

A sample of 0.5 ml for dansylation was placed in a 15 ml screw-capped vial, saturated with disodium carbonate, and mixed with 1.0 of 10 mg/ml dansyl chloride in acetone, and heated at 55° C. for two hours. After cooling to room temperature, 1.5 ml of deionized water was added to dabsylation mixture and heated one additional hour at 55° C. After cooling to room temperature, 1 ml of ethyl acetate was used to extract the dansylated ammonia. After phase separation between ethyl acetate and water for at least one hour, 0.5 ml of ethyl acetate was pipetted into a clean 3 ml vial and allowed to evaporate overnight. The solid dansylated ammonia was reconstituted with 0.5 ml of liquid mobile phase, and 50 $\mu$l was injected into the HPLC column and monitored at 325 nm. The flow rate of mobile phase was 1.5 ml for dansylated sample analysis.

Nitrates: Nitrate concentrations were determined spectrophotometrically at 410 nm using a chromotropic acid method, Hach Method 10020. The Hach Method 10020 involves reacting nitrate in the sample with chromotropic acid under strongly acidic conditions to yield a yellow product with a maximum absorbance at 410 nm.

Biomass Concentrations: The biomass concentrations were estimated as mixed liquor suspended solids (MLSS). A 20 mL sample was filtered through a tared glass filter, dried in a Lab Wave 9000, CEM microwave oven for 6 minutes, and re-weighed to determine MLSS as a weight difference over the sample volume.

It should be understood that the foregoing summary, detailed description, example and drawings of the invention are not intended to be limiting, but are only exemplary of the inventive features which are defined in the claims.

What is claimed is:

1. A process for biodegradation of an amine compound comprising the steps of:

(a) contacting the amine compound with a consortium of microorganisms effective for consuming carbon and nitrogen components of the amine compound under aerobic conditions, wherein the enzymatically degraded the amine compound forms an ammonia residue;

(b) nitrifying the ammonia residue under aerobic conditions, wherein the ammonia residue forms nitrite and nitrate residues; and, (c) denitrifying the compound with the addition of a supplementary carbon source under anoxic conditions.

2. The process of claim 1, wherein steps (a) and (b) are conducted simultaneously.

3. The process of claim 1, wherein the amine compound comprises diethylenetriamine (DETA).

4. The process of claim 1, wherein the amine compound comprises DS2.

5. The process of claim 1, wherein the amine compound further comprises ethylene glycol monomethyl ether (EGME).

6. The process of claim 1, wherein the consortium of microorganisms comprises *Bacillus circulans.*

7. The process of claim 1, wherein the consortium of microorganisms comprises the genera Nitrosomonas as a nitrifying agent for oxidizing ammonia to nitrite.

8. The process of claim 1, wherein the consortium of microorganisms comprises the genera Nitrobacter as a nitrifying agent for oxidizing nitrite to nitrate.

9. The process of claim 1, wherein the supplementary carbon source of step (c) is methanol.

10. The process of claim 1, wherein the supplementary carbon source of step (c) is sugar.

11. The process of claim 1, wherein the amine compound is an explosive-based composition.

12. The process of claim 11, wherein the explosive-based composition comprises propellent.

13. The process of claim 11, wherein the explosive-based composition comprises nitrocellulose.

14. The process of claim 1, wherein the aerobic conditions are maintained by bubbling oxygen into the amine compound and the consortium of microorganisms.

15. The process of claim 1, wherein the consortium of microorganism comprises *Bacillus circulans,* the genera Nitrosomonas, the genera Nitrobacter, and facultative heterotrophic denitrifiers.

16. The process of claim 1, wherein the contacting the amine compound is fed into a bioreactor.

17. The process of claim 7, wherein the contacting the amine compound is continuously fed into the bioreactor.

18. The process of claim 1, wherein the amine compound comprises from about 0.3% DS2 to about 0.7% DS2 and from about 10,000 mg/L to about 14,000 mg/L of microorganisms.

19. The process of claim 1, wherein the amine compound comprises from about 0.8% DS2 to about 1.2% DS2 and from about 18,000 mg/L to about 22,000 mg/L of microorganisms.

20. A composition of microorganisms comprising biologically pure cultures of *Bacillus circulans,* the genera Nitrosomonas, the genera Nitrobacter, and facultative heterotrophic denitrifiers effective to degrade DS2.

* * * * *